(12) United States Patent
Hughes, Jr.

(10) Patent No.: US 6,630,333 B1
(45) Date of Patent: Oct. 7, 2003

(54) SUBSTANTIALLY PURE REVERSE TRANSCRIPTASES AND METHODS OF PRODUCTION THEREOF

(75) Inventor: A. John Hughes, Jr., Germantown, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/533,548

(22) Filed: Mar. 23, 2000

Related U.S. Application Data
(60) Provisional application No. 60/126,050, filed on Mar. 23, 1999.

(51) Int. Cl.⁷ .............................................. C12N 9/12
(52) U.S. Cl. ....................................................... 435/194
(58) Field of Search ......................................... 435/194

(56) References Cited

U.S. PATENT DOCUMENTS

| | | | |
|---|---|---|---|
| 4,663,290 A | 5/1987 | Weis et al. | 435/253 |
| 4,683,195 A | 7/1987 | Mullis et al. | 435/6 |
| 4,683,202 A | 7/1987 | Mullis | 435/91 |
| 4,795,699 A | 1/1989 | Tabor et al. | 435/5 |
| 4,943,531 A | 7/1990 | Goff et al. | 435/194 |
| 5,017,492 A | 5/1991 | Kotewicz et al. | 435/252.3 |
| 5,244,797 A | 9/1993 | Kotewicz et al. | 435/194 |
| 5,405,776 A | 4/1995 | Kotewicz et al. | 435/252.3 |
| 5,409,818 A | 4/1995 | Davey et al. | 435/91.25 |
| 5,417,862 A | 5/1995 | Bergemann et al. | 210/626 |
| 5,455,166 A | 10/1995 | Walker | 435/91.2 |
| 5,498,523 A | 3/1996 | Tabor et al. | 435/6 |
| 5,516,292 A | 5/1996 | Steinman | 435/91.2 |
| 5,532,145 A | 7/1996 | Tessman et al. | 435/91.2 |
| 5,668,005 A | 9/1997 | Kotewicz et al. | 435/194 |
| 5,861,295 A | 1/1999 | Goldstein et al. | 435/194 |
| 5,989,819 A | * 11/1999 | Odawara | |
| 6,063,608 A | 5/2000 | Kotewicz et al. | 435/194 |
| 6,245,533 B1 | 6/2001 | Goldstein et al. | 435/91.1 |

FOREIGN PATENT DOCUMENTS

| | | |
|---|---|---|
| EP | 0 329 822 A2 | 8/1989 |
| EP | 0 534 858 A1 | 3/1993 |
| EP | 0 684 315 A1 | 11/1995 |
| WO | WO 86/06741 | 11/1986 |
| WO | WO 96/37781 | * 11/1996 |
| WO | WO 98/47912 | 10/1998 |

OTHER PUBLICATIONS

Schwartzberg, P., et al., "Construction and Analysis of Deletion Mutations in the pol Gene of Moloney Murine Leukemia Virus: A New Viral Function Required for Productive Infection," *Cell 37*:1043–1052, MIT Press (1984).

Skalka, A.M., and Goff, S., eds., in *Reverse Transcriptase,* Cold Spring Harbor Laboratory Press, Cold Spring Harbor, New York (1993).

Smith, J.K., et al., "Initiation of Plus–Strand DNA Synthesis During Reverse Transcriptase of an Avian Retrovirus Genome," *J. Virol. 49*:200–204, American Society for Microbiology (1984).

Soltis, D.A., and Skalka, A.M., "The α and β chains of avian retrovirus reverse transcriptase independently expressed in *Escherichia coli:* Characterization of enzymatic activities," *Proc. Natl. Acad. Sci. USA 85*:3372–3376, National Academy of Sciences of the USA (1988).

Srivastava, A. and Modak, M.J., "Reverse Transcriptase–associated RNase H. Part IV. Pyrophosphate does not inhibit RNase activity of AMV DNA polymerase," *Biochem. Biophys. Res. Commun. 91*:892–899, Academic Press, Inc. (1979).

Starnes, M.C., et al., "Enzyme Activity Gel Analysis of Human Immunodeficiency Virus Reverse Transcriptase," *J. Biol. Chem. 263*:5132–5134, American Society for Biochemistry and Molecular Biology, Inc. (1988).

Takatsuji, H., et al., "Expression of Cauliflower Mosaic Virus Reverse Transcriptase in Yeast," *Nature 319*:240–243, Macmillan Publishers Ltd. (1986).

Tanese, N., et al., "Expression of enzymatically active reverse transcriptase in *Escherichia coli,*" *Proc. Natl. Acad. Sci. USA 82*:4944–4948, National Academy of Sciences of the USA (1985).

Tanese, N., and Goff, S., "Fine–Structure Mutational Analysis of the Reverse Transcriptase Domain of Moloney Murine Leukemia Virus," Abstracts of papers presented at the 1987 meeting on RNA Tumor Viruses, May 19–May 24, 1987, Cold Spring Harbor Laboratory Press, Cold Spring Harbor, NY, p. 5 (1987).

Tanese, N., et al., "Expression of Reverse Transcriptase Activity of Human T–Lymphotrophic Virus Type III (HTLV–III/LAV) in *Escherichia coli,*" *J. Virol. 59*:743–745, American Society for Microbiology (1986).

Tanese, N., and Goff, S.P., "Domain structure of the Moloney murine leukemia virus reverse transcriptase Mutational analysis and separate expression of the DNA polymerase and RNase H activities," *Proc. Natl. Acad. Sci. USA 85*:1777–1781, National Academy of Sciences of the USA (1988).

(List continued on next page.)

*Primary Examiner*—Jon P. Weber
(74) *Attorney, Agent, or Firm*—Sterne, Kessler, Goldstein & Fox P.L.L.C.

(57) ABSTRACT

The present invention provides substantially pure reverse transcriptases, which are preferably substantially free from contamination with nucleic acids. The invention also provides methods for the production of these enzymes, and kits comprising these enzymes which may be used in synthesizing, amplifying or sequencing nucleic acid molecules including through the use of the polymerase chain reaction, particularly RT-PCR.

18 Claims, No Drawings

OTHER PUBLICATIONS

Telesnitsky, A., et al., "Defects in Moloney Murine Leukemia Virus Replication Caused by a Reverse Transcriptase Mutation Modeled on the Structure of *Escherichia coli* RNase H, " *J. Virol.* 66:615–622, American Society for Microbiology (1992).

Telenitsky, A., and Goff, S.P., "RNase H domain mutations affect the interaction between Moloney murine leukemia virus reverse transcriptse and its primer template," *Proc. Natl. Acad. Sci. USA* 90:1276–1280, National Academy of Sciences of the USA (1993).

Thimmig, R.L. and McHenry, C.S., "Human Immunodeficiency Virus Reverse Transcriptase," *J. Biol. Chem.* 268:16528–16536, American Society for Biochemistry and Molecular Biology, Inc. (1993).

Tisdale, M., et al., "Characterization of Human Immunodeficiency Virus Type 1 Reverse Transcriptase by Using Monoclonal Antibodies: Role of the C Terminus in Antibody Reactivity and Enzyme Function," *J. Virol.* 62:3662–3667, American Society for Microbiology (1988).

Tisdale, M., et al., "Structural characterization of HIV reverse transcriptase: A target for the design of specific virus inhibitors," *J. Antimicrobiol. Chemother.* 23(*Suppl* A):47–54, Academic Press, Inc. (1989).

Tisdale, M., et al., "Mutations within the RNase H domain of human immunodeficiency virus type 1 reverse transcriptase abolish virus infectivity," *J. Gen. Virol.* 72:59–66, Society for General Microbiology (1991).

Van Beveren, C. and Goulian, M., "Optical Conditions for Synthesis of Long Complementary DNA Product with Moloney Murine Leukemia Virus," *J. Virol.* 30:951–954, American Society for Microbiology (1979).

Verma, I.M., "Studies on Reverse Transcriptase of RNA Tumor Viruses III. Properties of Purified Moloney Murine Leukemia Virus DNA Polymerase and Associated RNase H," *J. Virol.* 15:843–854, American Society for Microbiology (1975).

Veronese, F., et al., "Characterization of Highly Immunogenic p66/p51 as the Reverse Transcriptase of HTLV–III/LAV," *Science* 231:1289–1291, Association for the Advancement of Science (1986).

Volkmann, S., et al., "Enzymatic Analysis of Two HIV–1 Reverse Transcriptase Mutants with Mutations in Carboxyl–terminal Amino Acid Residues Conserved among Retroviral Ribonucleases H," *J. Biol. Chem.* 268:2674–2683, American Society for Biochemistry and Molecular Biology, Inc. (1993).

Vos, P., et al., "AFLP: a new technique for DNA fingerprinting," *Nucl. Acids Res.* 23:4407–4414, Oxford University Press (1995).

Wang, L.–H., and Duesberg, P.H., "DNA Polymerase of Murine Sarcoma–Leukemia Virus: Lack of Detectable RNase H and Low Activity With Viral RNA and Natural DNA Templates," *J. Virol.* 12:1512–1521, American Society for Microbiology (1973).

Welsh, J., and McClelland, M., "Fingerprinting genomes using PCR with arbitrary primers," *Nucl. Acids Res.* 18:7213–7218, Oxford University Press (1990).

Williams, J.G.K., et al., "DNA polymorphisms amplified by arbitrary primers are useful as genetic markers," *Nucl. Acids Res.* 18:6531–6535, Oxford University Press (1990).

Wöhrl, B.M., et al., "Kinetic Analysis of Four HIV–1 Reverse Transcriptase Enzymes Mutated in the Primer Grip Region of p66," *J. Biol. Chem.* 272:17581–17587, American Society for Biochemistry and Molecular Biology, Inc. (1997).

Zhan, X., and Crouch, R.J., "The Isolated RNase H Domain in Murine Leukemia Virus Reverse Transcriptase," *J. Biol. Chem.* 272:22023–22029, American Society for Biochemistry and Molecular Biology, Inc. (1997).

Co–pending U.S. patent application Serial No. 09/229,967, filed Jan. 14, 1999.

Co–pending U.S. patent application Serial No. 09/245,025, filed Feb. 5, 1999.

Kacian, D.L. and Myers, J.C., "Synthesis of extensive, possibly complete, DNA copies of poliovirus RNA in high yields and at high specific activities," *Proc. Natl. Acad. Sci. USA* 73:2191–2195, National Academy of Sciences of the USA (1976).

Kamer, G., and Argos, P., "Primary structural comparison of RNA–dependent polymerase from plant, animal and bacterial viruses," *Nucl. Acids Res.* 12:7269–7282, IRL Press Limited (1984).

Kanaya, S., and Crouch, R.J., "Low Levels of RNase H Activity in *Escherichia coli* FB2 rnh Result from a Single–Base Change in the Structural Gene of RNase H," *J. Bacteriol.* 154:1021–1026, American Society for Microbiology (1983).

Kanaya, S., et al., "Identification of the Amino Acid Residues Involved in an Active Site of *Escherichia coli* Ribonuclease H by Site–directed Mutagenesis," *J. Biol. Chem. Chem.* 265:4615–4621, American Society for Biochemistry and Molecular Biology, Inc. (1990).

Katayanagi, K., et al., "Crystal Structures of Ribonuclease HI Active Site from *Escherichia coli*," *J. Biol. Chem.* 268:22092–22099, American Society for Biochemistry and Molecular Biology, Inc. (1993).

Kimmel, A.R., and Berger, S.L., "Preparation of cDNA and the Generation of cDNA Libraries: Overview," *Meth. Enzymol.* 152:307–389, Academic Press, Inc. (1987).

Klenow, H., and Henningsen, I., "Selective Elimination of the Exonuclease Activity of the Deoxyribonucleic Acid Polymerase from *Escherichia coli* B by limited Proteolysis," *Proc. Natl. Acad. Sci. USA* 65:168–175, National Academy of Sciences of the USA (1970).

Kotewicz, M.L. et al., "Cloning and overexpression of Moloney murine leukemia virus reverse transcriptase in *Escherichia coli*," *Gene* 35:249–258, Elsevier (1985).

Kotewicz, M.L., et al., "Isolation of cloned Moloney murine leukemia virus reverse transcriptase lacking ribonuclease H activity," *Nucl. Acids Res.* 16:265–277, IRL Press Limited (1988).

Lai, M.–H.T. and Verma, I.M., "Reverse Transcriptase of RNA Tumor Viruses. V. In Vitro Proteolysis of Reverse Transcriptase from Avian Myeloblastosis Virus and Isolation of a Polypeptide Manifesting Only RNase H Activity," *J. Virol.* 25:652–663, American Society for Microbiology (1978).

Lai, M.–H.T., et al., "Mammalian Retrovirus–Associated RNase H Is Virus Coded," *J. Virol.* 27:823–825, American Society for Microbiology (1978).

Larder, B., et al., "AIDS virus reverse transcriptase defined by high level expression in *Escherichia coli*," *EMBO J.* 6:3133–3137, IRL Press Limited (1987).

Larder, B.A., et al., "Site–Specific Mutagenesis of AIDS virus Reverse Transcriptase," *Nature* 327:716–717, Macmillan Publishers Ltd. (1987).

Laurent, S.J., and Vannier, F.S., "Permeabilization of *B subtilis* cells to macromolecules," *Biochimie* 59:747–750, Diffusion Masson (1977).

Lazzarini, R.A., and Johnson, L.D., "Regulation of Ribosomal RNA Synthesis in Cold–shocked *E. coli,*" *Nature New Biol.* 243:17–20, Macmillan Journals Limited (1973).

Levin, J.G., et al., "Murine Leukemia Virus Mutant with a Frameshift in the Reverse Transcriptase Coding Region: Implications for pol Gene Structure," *J. Virol.* 51:470–478, American Society for Microbiology (1984).

Levin, J.G., et al., "Functional Organization of the Murine Leukemia Virus Reverse Transcriptase: Characterization of a Bacterially Expressed AKR DNA Polymerase Deficient in RNase H Activity," *J. Virol.* 62:4376–4380, American Society for Microbiology (1988).

Lightfoote, M.M., et al., "Structural Characterization of Reverse Transcriptase and Endonuclease Polypeptides of the Acquired Immunodeficiency Syndrome Retrovirus," *J. Virol.* 60:771–775, American Society for Microbiology (1986).

Lori, F., et al., "Enzymatically Active Forms of Reverse Transcriptase of the Human Immunodeficiency Virus," *AIDS Res. Hum Retroviruses* 4:393–398, Mary Ann Liebert, Inc., Publishers (1988).

Lowe, D.M., et al., "HIV–1 Reverse Transcriptase: Crystallization and Analysis of Domain Structure by Limited Proteolysis," *Biochem.* 27:8884–8889, American Chemical Society (1988).

Maniatis, T., et al., "Synthesis of DNA," in *Molecular Cloning A Laboratory Manual,* Cold Spring Harbor Laboratory Press, Cold Spring Harbor, NY, p. 213, 231 (1982).

Margalith, M., et al., "Differential inhibition of DNA polymerase and RNase H activities of the reverse transcriptase by phosphonoformate," *Mol. Cell. Biochem.* 43:97–103, Martinus Nijhoff/Dr. W. Junk Publishers (1982).

McHenry, C.S., and Kornberg, A., "DNA Polymerase III Holoenzyme of *Escherichia coli,*" *J. Biol. Chem.* 252:6478–6484, American Society for Biochemistry and Molecular Biology, Inc. (1977).

Messer, L.I., et al., "Functional Analysis of Reverse Transcriptase by a Frameshift pol Mutant of Murine Leukemia Virus," *Virol.* 146:146–152, Academic Press, Inc. (1985).

Mizrahi, V., et al., "Recombinant HIV–1 Reverse Transcriptase Purification, Primary Structure, and Polymerase/Ribonuclease H Activities," *Arch. Biochem. Biophys.* 273:347–358, Academic Press, Inc. (1989).

Mizrahi, V., et al., "Site–directed mutagenesis of the conserved Asp–443 and Asp–498 carboxy–terminal residues of HIV–1 reverse transcriptase," *Nucl. Acids Res.* 18:5359–5363, Oxford University Press (1990).

Mizrahi, V., et al., "Mutagenesis of the Conserved Aspartic Acid 443, Glutamic Acid 478, Asparagine 494, and Aspartic Acid 498 Residues in the Ribonuclease H Domain of p66/p51 Human Immunodeficiency Virus Type 1 Reverse Transcriptase," *J. Biol. Chem.* 269:19245–19249, American Society for Biochemistry and Molecular Biology, Inc. (1994).

Modak, M.J., and Marcus, S.L., "Purification and Properties of Rauscher Leukemia Virus DNA Polymerase and Selective Inhibition of Mammalian Viral Reverse Transcriptase by Inorganic Phosphate," *J. Biol. Chem.* 252:11–19, American Society for Biochemistry and Molecular Biology, Inc. (1977).

Moelling, K., "Characterization of Reverse Transcriptase and RNase H from Friend–Murine Leukemia Virus," *Virol.* 62:46–59, Academic Press, Inc. (1974).

Moelling, K., "Further Characterization of the Friend Murine Leukemia Virus Reverse Transcriptase–RNase H Complex," *J. Virol.* 18:418–425, American Society for Microbiology (1976).

Moelling, K., and Friis, R.R., "Two Avian Sarcoma Cirus Mutants with Defects in the DNA Polymerase–RNase N Complex," *J. Virol.* 32:370–378, American Society for Microbiology (1979).

Mowshowitz, D.B., "Permeabilization of Yeast for Enzyme Assays: An Extremely Simple Method for Small Samples," *Anal. Biochem.* 70:94–99, Academic Press, Inc. (1976).

Müller, B., et al., "Co–expression of the Subunits of the Heterdimer of HIV–1 Reverse Transcriptase in *Escherichia coli,*" *J. Biol. Chem.* 264:13975–13978, American Society for Biochemistry and Molecular Biology, Inc. (1989).

Myers, J.C., et al., "Synthesis of full–length DNA copies of avian meyloblastosis virus RNA in high yields," *Proc. Natl. Acad. Sci. USA* 74:2840–2843, National Academy of Sciences of the USA (1977).

Myers, J.C., and Spiegelman, S., "Sodium pyrophosphate inhibition of RNA•DNA hybrid degradation by reverse transcriptase," *Proc. Natl. Acad. Sci. USA* 75:5329–5333, National Academy of Sciences of the USA (1978).

Najmudin, S., et al., "Crystal Structures of an N–terminal Fragment from Moloney Murine Leukemia Virus Reverse Transcriptase Complexed with Nucleic Acid: Functional Implications for template–primer Binding to the Fingers Domain," *J. Mol. Biol.* 296:613–632, Academic Press, Inc. (Feb. 2000).

Nakamura, H ., et al., "Structural models of ribonuclease H domains in reverse transcriptase from retroviruses," *Nucl. Acids Res.* 19:1817–1823, Oxford University Press (1991).

Old, R.W., and Primrose, S.B., "Principles of Gene Manipulation. An Introduction to Genetic Engineering," in *Studies in Microbiology,* Ch. 2, 2nd. ed., vol. 2, pp 26–27, University of California Press, Berkeley (1981).

Omer, C.A., and Faras, A.J., "Mechanism of Release of the Avian Retrovirus tRNA$^{Trp}$ Primer Molecule from Viral DNA by Ribonuclease H during Reverse Transcription," *Cell* 30:797–805, MIT Press (1982).

Oshima, T., and Imahori, K., "Description of *Thermus thermophilus* (Yoshida and Oshima) comb. Nov., a Nonsporulating Thermophilic Bacterium from a Japanese Thermal Spa," *Int. Syst. Bacteriol.* 24:102–112, International Association of Microbiological Societies (1974).

Prasad, V. and Goff, S., "Linker insertion mutagenesis of the human immunodeficiency virus reverse transcriptase expressed in bacteria: Definition of the minimal polymerase domain," *Proc. Natl. Acad. Sci. USA* 86:3104–3108, National Academy of Sciences of the USA (1989).

Putnam, S.L., and Koch, A.L., "Complications in the Simplest Cellular Enzyme Assay: Lysis of *Escherichia coli* for the Assay of β–Galactosidase," *Anal. Biochem.* 63:350–360, Academic Press, Inc. (1975).

Reardon, J., et al., "Human Immunodeficiency Virus Reverse Transcriptase," *J. Biol. Chem.* 266:14128–14134, American Society for Biochemistry and Molecular Biology, Inc. (1991).

Repaske, R., et al., "Inhibition of RNase H Activity and Viral Replication by Single Mutations in the 3' Region of Moloney Murine Leukemia Virus Reverse Transcriptase," *J. Virol.* 63:1460–1464, American Society for Microbiology (1989).

Resnick, R., et al., "Involvement of Retrovirus Reverse Transcriptase–Associated RNase H in the Initiation of Strong–Stop (+) DNA Synthesis and the Generation of the Long Terminal Repeat," *J. Virol.* 51:813–821, American Society for Microbiology (1984).

Rho, H.M., "Biochemical and Immunological Characterization of the DNA Polymerase and RNase H in Feline Leukemia Virus," *Korean J. Zool.* 22:141–152, The Zoological Society of Korea (1979).

Rho, H.M., and Gallo, R.C., "Biochemical and Immunological Properties of the DNA Polymerase and RNase H Activities of Purified Feline Leukemia Virus Reverse Transcriptase," *Cancer Lett.* 10:207–221, Elsevier/North Holland Scientific Publishers Ltd. (1980).

Roberts, J.D., and Lieberman, M.W., "Deoxyribonucleic Acid Repair Synthesis in Permeable Human Fibroblasts Exposed to Ultraviolet Radiation and N–Acetoxy-2-(acetylamino)fluorene," *Biochem.* 18:4499–4505, American Chemical Society (1979).

Roth, M., et al., "Purification and Characterization of Murine Retroviral reverse Transcriptase Expressed in *Escherichia coli*," *J. Biol. Chem.* 260:9326–9335, American Society for Biochemistry and Molecular Biology, Inc. (1985).

Sambrook, J., et al., "Harvesting and Lysis of the Bacteria," in *Molecular Cloning: A Laboratory Manual,* 2nd ed., Cold Spring Harbor, NY, Cold Spring Harbor Laboratory Press, pp. 1.22–1.23, 16.49 (1989).

Schatz, O., et al., "Point mutations in conserved amino acid residues within the C–terminal domain of HIV–1 reverse transcriptase specifically repress RNase H function," *FEBS Lett.* 257:311–314, Elsevier Science Publishers B.V. (1989).

Schatz, O., et al., "HIV–1 RT–associated ribonuclease H displays both endonuclease and 3'→5' endonuclease activity," *EMBO J.* 9:1171–1176, Oxford University Press (1990).

Shinnick, T.M., et al., "Nucleotide sequence of Moloney murine leukemia virus," *Nature* 293:543–548, Macmillan Publishers Ltd. (1981).

Schupp, J.M., et al., "Rapid Bacterial Permeabilization Reagent Useful for Enzyme Assays," *BioTechniques* 19:18–20, Eaton Publishing Company (1995).

Houts, G.E., et al., "Reverse Transcriptase from Avian Myeloblastosis Virus," *J. Virol.* 29:517–522, American Society for Microbiology (1979).

Huber, H.E., et al., "Human Immunodeficiency Virus 1 Reverse Transcriptase," *J. Biol. Chem.* 264:4669–4678, American Society for Biochemistry and Molecular Biology, Inc. (1989).

Hughes, A.J., Jr., et al., "Expression, Purification, and Characterization of an *Escherichia coli* Phage T5 DNA Polymerase 3'–5' Exonuclease Mutant," *J. Cell. Biochem. Suppl. 016(part B)*:84, Abstract No. F–538, Wiley–Liss, Inc. (1992).

Hizi, A., et al., "The Effects of Cysteine Mutations on the Reverse Transcriptases of Human Immunodeficiency Virus Types 1 and 2," *J. Biol. Chem.* 267:1293–1297, American Society for Biochemistry and Molecular Biology, Inc. (1992).

Hostomsky, Z., et al., "Ribonucleases H," in *Nucleases,* 2nd ed., Linn, S., and Roberts, R., eds., Cold Spring Harbor Laboratory Press, Cold Spring Harbor, N.Y., pp. 341–376 (1993).

Houdebine, L.–M., "Synthesis of DNA Complementary to the mRNAs for milk proteins by *E. coli* DNA polymerase I," *Nucl. Acids Res.* 3:615–630, IRL Press Limited (1976).

Hizi, A., and Joklik, W.K., "RNA–dependent DNA Polymerase of Avian Sarcoma Virus B77," *J. Biol. Chem.* 252:2281–2289, American Society for Biochemistry and Molecular Biology, Inc. (1977).

Hizi, A., et al., "Expression of soluable, enzymatically active, human immunodeficiency virus reverse transcriptase in *Escherichia coli* and analysis of mutants," *Proc. Natl. Acad. Sci. USA* 85:1218–1222, National Academy of Sciences of the USA (1988).

Hizi, A. et al., "Mutational Analysis of the Ribonuclease H Activity of Human Immunodeficiency Virus 1 Reverse Transcriptase," *Virol.* 175:575–580, Academic Press (1990).

Hansen, J., et al., "Identification and characterization of HIV–specific RNase H by monoclonal antibody," *EMBO J.* 7:239–243, IRL Press Limited (1988).

Heath, D.D., et al.,"PCR primed with VNTR core sequences yields species specific patterns and hypervariable probes," *Nucl. Acids Res.* 21:5782–5785, Oxford University Press (1993).

Hettwer, D., and Wang, H., "Protein Release from *Escherichia coli* Cells Permeabilized with Guanidine–HCl and Triton X100," *Biotechnol. Bioeng.* 33:886–895, John Wiley & Sons, Inc. (1989).

Green, M., and Gerard, G.F., "RNA–Directed DNA Polymerase—Properties and Functions in Oncogenic RNA Viruses and Cells," in *Progress in Nucleic Acid Research and Molecular Biology,* Cohn, W.E., ed., Academic Press, New York, vol. 14:187–334 (1974).

Gubler, U. and Hoffman, B.J., "A simple and very efficient method for generating cDNA libraries," *Gene* 25:263–269, Elsevier Science Publishers B.V. (1983).

Hansen, J., et al., "RNase H Activity Associated with Bacterially Expressed Reverse Transcriptase of Human T–cell Lymphotrophic Virus III/Lymphadenopathy–associated Virus," *J. Biol. Chem.* 262:12393–12396, American Society for Biochemistry and Molecular Biology, Inc. (1987).

Goff, S., "Genetic and Biochemical Approaches to the Study of Retroviral Replication: Role of the pol Gene Products of Moloney Murine Leukemia Virus," *DNA* 6, Speaker's Abstracts of the 7th Annual Congress, San Francisco, CA, Mar. 1–4, 1987.

Golomb, M. and Grandgenett, D.P., "Endonuclease Activity of Purified RNA–directed DNA Polymerase from Avian Myeloblastosis Virus," *J. Biol. Chem.* 254:1606–1613, American Society for Biochemistry and Molecular Biology, Inc. (1979).

Gorecki, M. and Panet, A., "Discrimination of DNA Polymerase and RNase H Activities in Reverse Transcriptase of Avian Myeloblastosis Virus," *Biochem.* 17:2438–2442, American Chemical Society (1978).

Grandgenett, D.P., et al., "Activation of an $Mg^{2+}$–Dependent DNA Endonuclease of Avian Myeloblastosis Virus αβ DNA Polymerase by In Vitro Proteolytic Cleavage," *J. Virol.* 33:264–271, American Society for Microbiology (1980).

Grandgenett, D.P., et al., "A Single Subunit from Avian Myeloblastosis Virus with Both RNA–Directed DNA Polymerase and Ribonuclease H Activity," *Proc. Natl. Acad. Sci. USA* 70:230–234, National Academy of Sciences of the USA (1973).

Grandgenett, D., et al., "Structural Characterization of the Avian Retrovirus Reverse Transcriptase and Endonuclease Domains," *J. Biol. Chem.* 260:8243–8249, American Society for Biochemistry and Molecular Biology, Inc. (1985).

Gerard, G.F., et al., "cDNA Synthesis by Moloney Murine Leukemia Virus RNase H–Minus Reverse Transcriptase Possessing Full DNA Polymerase Activity," *FOCUS* 14:91–93, Life Technologies, Inc. (1992).

Gerwin, B.I., et al., "Mutant of B–Tropic Murine Leukemia Virus Synthesizing an Altered Polymerase Molecule," *J. Virol.* 31:741–751, American Society for Microbiology (1979).

Goff, S.P., and Lobel, L.I., "Mutants of murine leukemia viruses and retroviral replication," *Biochim. Biophys. Acta* 907:93–123, Elsevier (1987).

Gerard, G.F. et al., "Influence on Stability in *Escherichia coli* of the Carboxy–Terminal Structure of Cloned Moloney Murine Leukemia Virus Reverse Transcriptase," *DNA* 5:271–279, Mary Ann Liebert, Inc., Publishers (1986).

Gerard, G.F., "Synthesis of High Specific Activity cDNA," *FOCUS* 10:12–13, Life Technologies, Inc. (1988).

Gerard, G., et al., "cDNA Synthesis by Cloned Moloney Murine Leukemia Virus Transcriptase Lacking RNase Activity," *FOCUS* 11:66–69, Life Technologies, Inc. (1989).

Gerard, G.F., "Multiple RNase H Activities in Mammalian Type C Retravirus Lysates," *J. Virol.* 26:16–28, American Society for Microbiology (1978).

Gerard, G.F., "Mechanism of Action of Moloney Murine Leukemia Virus RNase H III," *J. Virol* 37:748–754, American Society for Microbiology (1981).

Gerard, G.F., "Comparison of cDNA Synthesis by Avian and Cloned Murine Reverse Transcriptase," *FOCUS* 7:1–3, Life Technologies, Inc. (1985).

Georgiadis, M., et al., "Mechanistic implications from the structure of a catalytic fragment of Moloney murine leukemia virus reverse transcriptase," *Structure* 3:879–892, Current Biology Ltd. (1995).

Gerard, G.F., et al., "Poly (2'methylcytidylate)•Oligodeoxyguanylate as a Template for the Ribonucleic Acid Directed Deoxyribonucleic Acid Polymerase in Ribonucleic Acid Tumor Virus Particles and a Specific Probe for the Ribonucleic Acid Directed Enzyme in Transformed Murine Cells," *Biochem.* 13:1632–1641, American Chemical Society (1974).

Gerard, G.F. and Grandgenett, D.P., "Purification and Characterization of the DNA Polymerase and RNase H Activities in Moloney Murine Sarcoma–Leukemia Virus," *J. Virol.* 15:785–797, American Society for Microbiology (1975).

Finston, W.I. and Champoux, J.J., "RNA–Primed Initiation of Moloney Murine Leukemia Virus Plus Strands by Reverse Transcriptase In Vitro," *J. Virol.* 51:26–33, American Society for Microbiology (1984).

Freeman–Wittig, M.–J., et al., "Differential Effects of Captan on DNA Polymerase and Ribonuclease H Activities of Avian Myeloblastosis in Virus Reverse Transcriptase," *Biochem.* 25:3050–3055, American Chemical Society (1986).

Freeman–Wittig, M.–J., and Lewis, R.A., "Captan binding to avian myeloblastosis virus reverse transcriptase and its effect on RNase H activity," *Mol. Cell Biochem.* 94:9–17, Kluwer Academic Publishers (1990).

Dudding, L.R., et al., "Analysis of the RNA– and DNA–Dependent DNA Polymerase Activities of Point Mutants of HIV–1 Reverse Transcriptase Lacking Ribonuclease H Activity," *Biochem.* 30:10498–10506, American Chemical Society (1991).

Farmerie, W.G., et al., "Expression and Processing of the Aids Virus Transcriptase in *Escherichia coli*," *Science* 236:305–308, Association for the Advancement of Science (1987).

Felix, H., "Permeabilized Cells," *Anal. Biochem.* 120:211–234, Academic Press, Inc. (1982).

Crouch, R.J., and Dirksen, M.–L., "Ribonuclease H," in *Nucleases,* Linn, S.M., and Roberts, R.J., eds., Cold Spring Harbor Laboratory Press, Cold Spring Harbor, NY, pp. 211–241 (1982).

Cull, M., and McHenry, C.S., "Preparation of Extracts from Prokaryotes," *Meth. Enzymol.* 182:153, Academic Press, Inc. (1990).

DeStefano, J.J., et al., "Polymerization and RNase H Activities of the Reverse Transcriptase from Avian Myeloblastosis, Human Immunodeficiency, and Moloney Murine Leukemia Viruses Are Functionally Uncoupled," *J. Biol. Chem.* 266:7423–7431, American Society for Biochemistry and Molecular Biology, Inc. (1991).

Caetano–Anollés, G., et al., "DNA Amplification Fingerprinting Using Very Short Arbitrary Oligonucleotide Primers," *Bio/Technol.* 9: 553–557, Nature Publishing Co. (1991).

Chattopadhyay, D., et al., Resolution of Microheterogeneity Associated with Recombinant HIV–1 Heterodimeric Reverse Transcriptase, *Prot. Expr. Purif.* 3:151–159, Academic Press, Inc. (1992).

Copeland, T.D., et al., "Amino– and Carboxyl–Terminal Sequence of Moloney Murine Leukemia Virus Reverse Transcriptase," *Virol.* 143:676–679, Academic Press, Inc. (1985).

Brewer, L.C. and Wells, R.D., "Mechanistic Independence of the Avian Myeloblastosis Virus DNA Polymerase and Ribonuclease H," *J. Virol* 14:1494–1502, American Society for Microbiology (1974).

Brock, T.D., and Freeze, H., "*Thermus Aquaticus* gen. N. and sp. N., a Non–sporulating Extreme Thermophile," *J. Bacteriol.* 98:289–297, American Society for Microbiology (1969).

Buiser, R.G., et al., "Requirements for the Catalysis of Strand Transfer Synthesis by Retroviral DNA Polymerases," *J. Biol. Chem.* 266: 13103–13109, American Society for Biochemistry and Molecular Biology, Inc. (1991).

Bathurst, I.C., et al., "Characterization of the Human Immunodeficiency Virus Type–1 Reverse Transcriptase Enzyme Produced in Yeast," *Biochem Biophys Res. Commun.* 171:589–595, Academic Press, Inc. (1990).

Berger, S.L., et al., "Reverse Transcriptase and Its Associated Ribonuclease H: Interplay of Two Enzyme Activities Controls the Yield of Single-Stranded Complementary Deoxyribonucleic Acid," *Biochem.* 22:2365–2372, American Chemical Society (1983).

Blain, S.W., and Goff, S.P., "Nuclease Activities of Moloney Murine Leukemia Virus Reverse Transcriptase," *J. Biol. Chem.* 268:23585–23592, American Society for Biochemistry and Molecular Biology, Inc. (1993).

Amos, H., et al., "Protein Synthesis in Sonically Damaged *Escherichia coli,*" *J. Bacteriol.* 94:232–240, American Society for Microbiology (1967).

Ausubel, F.M., et al., "Preparation of Bacterial RNA," in *Current Protocols in Molecular Biology,* New York, John Wiley & Sons, pp. 4.4.1–4.4.7 (1993).

Barr, P.J., et al, "Expression of Active Human Immunodeficiency Virus Reverse Transcriptase in *Saccharomyces Cerevisiae,*" *Bio/Technology* 5:486–489, Nature Publishing Co. (1987).

Reddy, K.J. and Gilman, M., "Preparation of Bacterial RNA," in *Current Protocols in Molecular Biology,* Ausubel, F.M. et al., eds., pp. 4.4.1–4.4.7, New York, NY, John Wiley & Sons, Inc. (1993).

Co-pending U.S. patent application Serial No. 09/866,816, Goldstein et al., filed May 30, 2001.

McCoy, J. and LaVallie, E., "*E. Coli* Lysis Using a French Pressure Cell," in *Current Protocols in Molecular Biology,* Ausubel, F.M. et al., eds. pp. 16.8.6–16.8.14, New York, NY, John Wiley and Sons, Inc. (1994).

Meyer, W. et al., "Purification, Cloning, and Sequencing of Archaebacterial Pyrophosphatase from the Extreme Thermoacidophile *Sulfolobus acidocaldarius,*" *Arch. Biochem. Biophys.* 319:149–156, Academic Press, Inc. (1995).

Park, J.H., "Purification and characterization of *Thermus caldophilus* GK24 DNA polymerase," *Eur. J. Biochem.* 214:135–140, FEBS (1993).

Harrell II, R.A. and Hart, R.P., "Rapid Preparation of *Thermus Flavus* DNA Polymerase," *PCR Meth. Appl.* 3:372–375, Cold Spring Harbor Laboratory Press (1994).

* cited by examiner

US 6,630,333 B1

SUBSTANTIALLY PURE REVERSE TRANSCRIPTASES AND METHODS OF PRODUCTION THEREOF

This application claims the benefit of Provisional application Ser. No. 60/126,050, filed Mar. 23, 1999.

FIELD OF THE INVENTION

The present invention is in the fields of molecular biology, protein chemistry and protein purification. Specifically, the invention provides compositions comprising reverse transcriptases (RTs) and methods for the production of such reverse transcriptase enzymes. Such methods provide for reverse transcriptases that are substantially free from contamination by nucleic acids and other unwanted materials or proteins. Compositions comprising the reverse transcriptase enzymes of the present invention may be used in a variety of applications, including synthesis, amplification and sequencing of nucleic acids.

BACKGROUND AND SUMMARY OF THE INVENTION

A variety of techniques may be employed to facilitate the preparation of intracellular proteins from microorganisms. Typically, the initial steps in these techniques involve lysis or rupture of the bacterial cells, to disrupt the bacterial cell wall and allow release of the intracellular proteins into the extracellular milieu. Following this release, the desired proteins are purified from the extracts, typically by a series of chromatographic steps.

Several approaches have proven useful in accomplishing the release of intracellular proteins from bacterial cells. Included among these are the use of chemical lysis, physical methods of disruption, or a combination of chemical and physical approaches (reviewed in Felix, H., *Anal. Biochem.* 120:211–234 (1982)).

Chemical methods of disruption of the bacterial cell wall that have proven useful include treatment of cells with organic solvents such as toluene (Putnam, S. L., and Koch, A. L., *Anal. Biochem.* 63:350–360 (1975); Laurent, S. J., and Vannier, F. S., *Biochimie* 59:747–750 (1977); Felix, H., *Anal. Biochem.* 120:211–234 (1982)), with chaeotropes such as guanidine salts (Hettwer, D., and Wang, H., *Biotechnol. Bioeng.* 33:886–895 (1989)), with antibiotics such as polymyxin B (Schupp, J. M., et al., *BioTechniques* 19:18–20 (1995); Felix, H., *Anal. Biochem.* 120:211–234 (1982)), or with enzymes such as lysozyme or lysostaphin (McHenty, C. S., and Kornberg, A., *J. Biol. Chem.* 252(18):6478–6484 (1977); Cull, M., and McHenry, C. S., *Meth. Enzymol.* 182:147–153 (1990); Hughes, A. J., Jr., et al., *J. Cell Biochem. Suppl.* 016 (Part B):84 (1992); Sambrook, J., et al., in *Molecular Cloning: A Laboratory Manual*, 2$^{nd}$ ed., Cold Spring Harbor, N.Y.; Cold Spring Harbor Laboratory Press, p. 17–38 (1989); Ausubel, F. M., et al.; in *Current Protocols in Molecular Biology*, New York: John Wiley & Sons, p. 4.4.1–4.47 (1993)). The effects of these various chemical agents may be enhanced by concurrently treating the bacterial cells with detergents such as Triton X-100®, sodium dodecylsulfate (SDS) or Brij 35 (Laurent, S. J., and Vannier, F. S., *Biochimie* 59:747–750 (1977); Felix, H., *Anal. Biochem.* 120:211–234 (1982); Hettwer, D., and Wang, H., *Biotechnol. Bioeng*, 33:886–895 (1989); Cull, M., and McHenry, C. S., *Meth. Enzymol.* 182:147–153 (1990); Schupp, J. M., et al., *BioTechniques* 19:18–20 (1995)), or with proteins or protamines such as bovine serum albumin or spermidine (McHenry, C. H. and Kornberg, A., *J. Biol. Chem.* 252(18): 6478–6484(1977); Felix, H., *Anal. Biochem.* 120:211–234 (1982); Hughes, A. J., Jr., et al., *J. Cell Biochem. Suppl.* 0 16 (Part B):84 (1992)).

In addition to these various chemical treatments a number of physical methods of disruption have been used. These physical methods include osmotic shock, e.g., suspension of the cells in a hypotonic solution in the presence or absence of emulsifiers (Roberts, J. D., and Lieberman, M. W., *Biochemistry* 18:4499–4505 (1979); Felix, H., *Anal. Biochem.* 120:211–234 (1982)), drying (Mowshowitz, D. B., *Anal. Biochem.* 70:94–99 (1976)), bead agitation such as ball milling (Felix, H., *Anal. Biochem.* 120:211–234 (1982); Cull, M., and McHenry, C. S., *Meth. Enzymol.* 182:182:147–153 (1990)), temperature shock, e.g., freeze-thaw cycling (Lazzarini, R. A., and Johnson L. D., *Nature New Biol.* 243:17–20 (1975); Felix, H., *Anal, Biochem.* 120:211234 (1982)), sonication (Amos, H., et al., *J. Bacteriol.* 94:232–240 (1967); Ausubel, F. M., et al., in *Current Protocols in Molecular Biology*, New York:John Wiley & Sons, pp. 4.4.1–4.47 (1993)) and pressure disruption, e.g., use of a french pressure cell (Ausubel, F. M., et al., in *Current Protocols in Molecular Biology*, New York:John Wiley & Sons, pp. 16.8.6–16.8.8 (1993)). Other approaches combine these chemical and physical methods of disruption, such as lysozyme treatment followed by sonication or pressure treatment, to maximize cell disruption and protein release (Ausubel, F. M., et al., in *Current Protocols in Molecular Biology*, New York:John Wiley & Sons, pp. 4.4.1–4.47 (1993)).

These disruption approaches have several advantages, including their ability to rapidly and completely (in the case of physical methods) disrupt the bacterial cell such that the release of intracellular proteins is maximized. In fact, these approaches have been used in the initial steps of processes for the purification of a Variety of bacterial cytosolic enzymes, including natural and recombinant proteins from mesophilic organisms such as *Escherichia coli, Bacillus subtilis* and *Staphylococcus aureus* (Laurent, S. J., and Vannier, F. S., *Biochimie* 59:747–750 (1977); Cull, M., and McHenry, C. S., *Meth. Enzymol.* 182:147–153 (1990); Hughes, A. J., Jr., et al., *J. Cell Biochem. Suppl.* 0 16 (Part B): 84 (1992); Ausubel, F. M., et al., in *Current Protocols in Molecular Biology*, New York: John Wiley & Sons, pp. 4.4.1–4.47 (1993)), as well as phosphatases, restriction enzymes, DNA or RNA polymerases and other proteins from thermophilic bacteria and archaea.

However, these methods possess distinct disadvantages as well. For example, the physical methods by definition involve shearing and fracturing of the bacterial cell walls and plasma membranes. These processes thus result in extracts containing large amounts of particulate matter, such as membrane or cell wall fragments, which must be removed from the extracts, typically by centrifugation, prior to purification of the enzymes. This need for centrifugation limits the batch size capable of being processed in a single preparation to that of available centrifuge space; thus, large production-scale preparations are impracticable if not impossible. Furthermore, physical methods, and may chemical techniques, typically result in the release from the cells not only of the desired intracellular proteins, but also of undesired nucleic acids and membrane lipids (the latter particularly resulting when organic solvents are used). These undesirable cellular components also complicate the subsequent processes for purification of the desired proteins, as they increase the viscosity of the extracts (Sambrook, J., et al., in: *Molecular Cloning: A Laboratory Manual*, 2$^{nd}$ ed., Cold Spring Harbor, N.Y.: Cold Spring Harbor Laboratory Press, p. 17–38 (1989); Cull, M., and McHenry, C. S., *Meth. Enzynol.* 182:147–153 (1990)), and bind with high avidity and affinity to nucleic acid-binding proteins such as DNA polymerases, RNA polymerases and restriction enzymes.

One problem associated with these approaches is that the enzyme preparations are typically contaminated with nucleic acids (e.g., RNA and DNA). This contaminating nucleic acid may come not only from the organisms which are the source of the enzyme, but also from unknown organisms present in the reagents and materials used to purify the enzyme after its release from the cells. Since reverse transcriptase enzymes are routinely used in techniques of amplification and synthesis of nucleic acid molecules (e.g., the Polymerase Chain Reaction (PCR), particularly RT-PCR) the presence of contaminating DNA or RNA in the enzyme preparations is a significant problem since it can give rise to spurious amplification or synthesis results. Thus, a need exists for preparation of reverse transcriptase enzymes that are substantially free of contamination by nucleic acids.

Instead of attempting to remove nucleic acids from preparations of reverse transcriptase enzymes, a more reasonable and successful approach would be to prevent contamination of the enzymes by nucleic acids from the outset in the purification process. Such an approach would be two-pronged: 1) preventing release of nucleic acids from the bacterial cells during permeabilization of the cells to release the enzymes; and 2) preventing contamination of the enzymes during the purification process itself. Furthermore, an optimal method would obviate the need for centrifugation in the process, thus allowing large-scale, and even continuous, production of nucleic acid-free reverse transcriptase enzymes. The present invention provides such methods, and reverse transcriptase enzymes produced by these methods.

The present invention generally provides methods of making a reverse transcriptase enzyme comprising permeabilizing a cellular source of reverse trans criptase (e.g., bacterial cells) to form spheroplasts or protoplasts and isolating the reverse transcriptase enzyme. Preferably, the methods are conducted under conditions favoring the partitioning of nucleic acids from the reverse transcriptase enzyme. In particular, the invention relates to a method for isolation or purification of reverse transcriptases comprising cell permeabilization, filtration and isolation.

The invention is particularly directed to methods wherein the permeabilization of the cells is accomplished by contacting the cells with an aqueous solution comprising at least one of: a chaeotropic agent, preferably a guanidine salt and most preferably guanidine hydrochloride; and/or a nonionic detergent, preferably Triton X-100 and/or sodium deoxycholic acid. The invention is further directed to such methods wherein the conditions favoring the partitioning of nucleic acids from the reverse transcriptase enzyme comprise formation of an filtrate (e.g., ultrafiltrate) by filtration (e.g., microfiltration) of the cellular source subjected to permeabilization (particularly of the spheroplasts or protoplasts) through a semi-permeable membrane, which is preferably a hydrophilic dialysis membrane, preferably in the presence of a salt, preferably ammonium sulfate, and purification or isolation of the reverse transcriptase enzyme from the filtrate, preferably by chromatography using sterile materials. The invention is particularly directed to such methods wherein bacterial cells providing the reverse transcriptase enzyme are used, preferably prokaryotic cells such as those of species of the genera Escherichia (preferably *E. coli*), Bacillus, Serratia, Salmonella, Staphylococcus, Streptococcus, Clostridium, Chlamydia, Neisseria, Treponema, Klebsiella, Mycoplasma, Borrelia, Legionella, Pseudomonas, Mycobacterium, Helicobacter, Erwinia, Agrobacterium, Rhizobium, Xanthomonas and Streptomyces. In another aspect, the cellular source of reverse transcription is a recombinant cellular source.

The invention also provides the reverse transcriptase enzymes, or mutants, derivatives or fragments thereof, that are made according to the methods provided. The invention is also directed to methods for amplifying or synthesizing a nucleic acid molecule comprising contacting a nucleic acid molecule (e.g., template) with an reverse transcriptase made according to the methods of the present invention under conditions to make a first nucleic acid molecule complementary to all or a portion of the template. Such synthesis or amplification may further comprise incubating the reaction with one or more polymerases (DNA polymerases, preferably thermostable DNA polymerases such as Tne, Tma, Taq etc. or mutants, derivatives or fragments thereof) under conditions sufficient to make a second nucleic acid molecule complementary to all or a portion of the first nucleic acid molecule.

The invention also provides kits for amplifying or synthesizing nucleic acid molecules comprising a carrier means having in close confinement therein one or more container means, wherein said kit may comprise at least one component selected from one or more reverse transcriptases produced according to the invention, one or more polymerases (e.g., DNA polymerases), one or more nucleotides or derivatives thereof, one or more primers, and one or more synthesis or amplification reaction buffers.

Other features and advantages of the present invention will be apparent to those skilled in the art from the following description of the preferred embodiments and from the claims.

DETAILED DESCRIPTION OF THE INVENTION

Overview

The present invention in a preferred aspect provides reverse transcription enzymes that are substantially pure and more preferably reverse transcriptases that are substantially free of nucleic acids. As used herein, the term "substantially free of nucleic acids" means an enzyme composition that comprises no nucleic acids, or that comprises nucleic acids below the level of detection, when assayed by standard biochemical assays for nucleic acids. Such assays may include gel electrophoresis (e.g., agarose gel electrophoresis coupled with nucleic acid staining such as ethidium bromide, acridine orange or Hoechst staining), spectrophotometry (e.g., ultraviolet, atomic absorption, NMR or mass spectrometry), chromatography (liquid, gas, HPLC or FPLC), or by functional assays for nucleic acids detection such as amplification. An example of such functional assay is based on measuring incorporation of labeled nucleotides (e.g., radio labeled, enzyme labels, chemiluminescent labels, etc.) by the enzyme preparation in a "no-template" nucleic acid amplification reaction. These biochemical and functional assays are described in more detail below and in Example 3. The invention also provides methods for the production of these enzymes, and compositions and kits comprising these enzymes which may be used in synthesis or amplifying nucleic acid molecules, including through use of the polymerase chain reaction (PCR).

Briefly summarized, the present invention utilizes a scheme comprising permeabilization of cells (preferably bacterial cells) to form spheroplasts or protoplasts, filtration (e.g., microfiltration) of the spheroplasts or protoplasts to form a filtrate (e.g., microfiltrate), ultrafiltration of the filtrate to form an ultrafiltrate, and purification of the enzyme from the ultrafiltrate, preferably by conventional liquid chromatography. The present invention 1) provides a method of large-scale (>20 million unit) production of reverse transcriptases, including MMLV-RT and mutants or derivatives thereof; and 2) provides a scalable method for the production of any desirable quantity of the desired enzyme.

The present methods are based in particular upon an optimized method of chemical permeabilization of cells (preferably bacterial cells), which preferably strips the cell wall and yields spheroplasts (although conditions to merely permeabilize the cell wall to form protoplasts may equally be used), and an optimized method of filtration of the spheroplasts or protoplasts under conditions favoring the release of reverse transcriptase enzymes, but inhibiting the release of nucleic acids, from the spheroplasts or protoplasts. The permeabilization process has been optimized to allow intracellular enzymes, particularly reverse transcriptases, to permeate or cross the spheroplast or protoplast membrane while preventing the cellular nucleic acids (DNA and/or RNA) from entering the permeation buffer. This approach provides an initial extract that is enriched in enzyme and that is relatively free of nucleic acids. The extract is then subjected to filtration under conditions (including precise definition of the variables of salt, pH, and choice of membrane chemistry) favoring release of the enzyme from the spheroplasts or protoplasts while preventing cells, cell debris and/or nucleic acids from crossing the filtration membrane barriers. Following filtration (which may include microfiltration and/or ultrafiltration), reverse transcriptase enzymes may be purified or isolated by standard techniques such as chromatography or electrophoresis, to provide enzyme preparations of the invention.

Sources of Reverse Transcriptase Enzymes

Any reverse transcriptase enzymes may be prepared according to the methods of the present invention from a variety of prokaryotic and eukaryotic cells including bacteria that are commercially available (for example, from American Type Culture Collection (ATCC), Rockville, Md. and the Collection, Agricultural Research Culture Collection (NRRL), Peoria, Ill.). Examples of bacterial deposits as sources of RTs include ATCC deposit no. 67007 (M-MLV RT H+), ATCC deposit no. 67555 (M-MLV H−), NRRL B-21790 (AMV RT αH+/βH−), and NRRL B-21679 (RSV RT αH+/βH−).

Enzymes prepared in accordance with the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, and mutants, fragments, variants or derivatives thereof (see WO 98/47912, U.S. Pat. Nos. 5,668,005, and 5,017,492). As will be understood by one of ordinary skill in the art, modified reverse transcriptases may be obtained by recombinant or genetic engineering techniques that are routine and well-known in the art. Mutant reverse transcriptases can, for example, be obtained by mutating the gene or genes encoding the reverse transcriptase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases of the invention. Fragments of reverse transcriptases may be obtained by deletion mutation by recombinant techniques that are routine and well-known in the art, or by enzymatic digestion of the reverse transcriptase(s) of interest using any of a number of well-known proteolytic enzymes.

Preferred enzymes which may be prepared according to the invention include those that are reduced or substantially reduced in RNase H activity. Such enzymes that are reduced or substantially reduced in RNase H activity may be obtained by mutating the RNase H domain within the reverse transcriptase of interest, preferably by one or more point mutations, one or more deletion mutations, and/or one or more insertion mutations as described above. By an enzyme "substantially reduced in RNase H activity" is meant that the enzyme has less than about 30%, less than about 25%, less than about 20%, more preferably less than about 15%, less than about 10%, less than about 7.5%, or less than about 5%, and most preferably less than about 5% or less than about 2%, of the RNase H activity of the corresponding wild type or RNase H+ enzyme such as wild type Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for sample, in U.S. Pat. No, 5,244,797, in Kotewicz, M. L., et al., *Nucl. Acids Res.* 16:265 (1988), in Gerard, G. F., et al., *FOCUS* 14(5): 91 (1992), in WO 98/47912, and in U.S. Pat. No. 5,668,005, the disclosures of all of which are fully incorporated herein by reference.

Particularly preferred enzymes for use in the invention include, but are not limited to M-MLV H− reverse transcriptase, RSV H− reverse transcriptase, AMV H− reverse transcriptase, RAV H− reverse transcriptase, MAV reverse transcriptase and HIV H− reverse transcriptase (see WO 98/47912). It will be understood by one of ordinary skill, however, that any enzyme capable of producing a DNA molecule from a ribonucleic acid molecule (i.e., having reverse transcriptase activity) that is reduced or not reduced in RNase H activity may be equivalently prepared in accordance with the invention.

It will be understood by one of ordinary skill in the art, however, that any cell, virus, microorganism or bacteria (including prokaryotic and eukaryotic) may be used as a source for preparation of reverse transcriptase enzymes (e.g., cellular source of RT) according to the methods of the present invention. Preferably, recombinant cells (prokaryotic or eukaryotic) are used as a source of the reverse transcriptases in the methods of the invention. Such recombinant cells may be prepared by recombinant DNA techniques that are familiar to one or ordinary skill in the art (see e.g., Kotewicz, M. L., et al., *Nucl. Acids Res.* 16:265 (1988); Soltis, D. A., and Skalka, A. M., *Proc. Natl. Acad. Sci. USA* 85:3372–3376 (1988)). Such sources of reverse transcriptases may be grown according to standard microbiological techniques, using culture media and incubation conditions suitable for growing active cultures of the particular species that are well-known to one of ordinary skill in the art (see, e.g., Brock, T. D., and Freeze, H., *J. Bacteriol.* 98(1):289–297 (1969); Oshima, T., and Imahori, K., *Int. J. Syst. Bacteriol.* 24(1):102–112 (1974)).

Permeabilization of Cells

In the initial steps of the present methods, a cellular source of reverse transcriptase is treated under conditions to allow the release of the reverse transcriptase from the cell and preferably to retain nucleic acids in the cell. Such conditions may include permeabilizing the cells by stripping away the cell walls and converting the cells into spheroplasts or permeabilizing the cell (making openings in the cell wall without totally removing it) to convert the cells into protoplasts. Such conditions may include chemical and/or enzymatic (e.g., lysozyme) treatment, although a variety of other techniques may be used for this permeabilization. The production of substantially nucleic acid-free enzymes by the present invention preferably uses a permeabilization method which will produce protoplast or spheroplasts that retain substantially all the nucleic acids within the spheroplast or protoplasts while allowing intracellular proteins (including enzymes) to move across the spheroplast or protoplast membrane. All procedures from permeabilization to final purification of the enzymes should be carried out at temperatures below normal room temperature, preferably at about 1–10° C., more preferably at about 2–8° C., and most preferably at about 2–6° C., to prevent enzyme denaturation and loss of activity. Furthermore, all materials used throughout the present methods (i.e., reagents, salts, chromatography resins, equipment) should be sterilized by heat or barrier sterilization techniques (as appropriate to the material to be sterilized), to prevent the contamination of the reverse transcriptase enzymes with nucleic acids or other unwanted contaminants.

This permeabilization is preferably accomplished by suspension of the cells in an aqueous solution comprising at least one or more chaeotropic agents and/or nonionic detergent. According to a preferred embodiment, this permeabilization is preferably accomplished by suspension of the cells in an aqueous solution comprising at least two nonionic detergents. Chaeotropic agents preferable for use in the methods of the present invention include salts of guanidine or urea, most preferably guanidine hydrochloride. Any nonionic detergent may be used; most preferable are octylphenoxy-polyethoxyethanol nonionic surfactant (TRITON X-100®), Brij 35, Tween 20 and Nonidet P-40 (NP-40®), although other nonionic surfactants and mixtures thereof, such as N-alkylglucosides, N-alkylmaltosides, glucamides, digitonin, deoxycholate, 3-[3-cholamidopropyl)dimethyl-ammonium]-1-propane-sulfonate (CHAPS) or cetyltrimethyl-ammonium-bromide (CTAB) may also be used in the present compositions. Reagents such as chaeotropes, detergents, buffer salts, etc., are available commercially, for example from Sigma Chemical Co. (St. Louis, Mo.).

For permeabilization, the cells are preferably suspended in a buffered salt solution containing the chaeotrope(s) and/or the detergent(s). Preferably, the solution is an aqueous solution with a distilled, deionized water (dH$_2$O) base consisting of bis-trishydroxymethylaminomethane (BisTRIS® base) at a concentration of about 25–500 mM, preferably about 50–250 mM, more preferably about 50–150 mM, and most preferably about 100 mM, at a pH of about 7.0–9.0, preferably about 7.0–8.5, more preferably about 7.0–8.0, more preferably about 7.0–7.5 and most preferably about 7.0 (pH at about 20–25° C.). The concentration of the chaeotrope in the solution is preferably about 300–1000 mM, more preferably about 500–750 mM, and most preferably about 600 mM. The concentration of the nonionic detergent is preferably about 1–10% (vol/vol), more preferably about 2–8% and most preferably about 2–5%. Within the context of the present invention, one or more chaeotropic agents and/or nonionic detergents may be used within the concentration ranges specified. The permeabilization buffer solution may also comprise other components, such as protease inhibitors (e.g., phenylmethylsulfonylfluoride, added at a final concentration of about 0.5 mM), reducing agents (e.g., β-mercaptoethanol or most preferably dithiothreitol at a final concentration of about 1 mM), and chelating agents (e.g., disodium ethylenediaminetetraacetic acid (Na$_2$EDTA), most preferably at a concentration of about 10 mM); this buffer composition is referred to hereinafter as "permeabilization buffer." It will be understood by one of ordinary skill in the art, however, that other suitable buffer compositions may be substituted with equivalent effect in the permeabilization process.

For permeabilization, the cells are preferably suspended in permeabilization buffer at a concentration of about 50–1000 g (wet weight) of cells per liter of solution, preferably about 100–500 g/L, and most preferably about 250 g/L (cell density of about $1-5\times10^{10}$ cells/gram, preferably about $2-5\times10^{10}$ cells/gram, and most preferably about $2.5\times10^{10}$ cells/gram). The cell suspension is gently stirred, preferably via magnetic or impeller stirring, in such a way as to prevent shearing and rupture of the cells. After about 30–60 minutes, most preferably about 45 minutes, a protein-extracting salt is added to the suspension to enhance the permeation of the intracellular enzymes across the spheroplast or protoplast membranes. Although any salt may be used in the present invention (except salts of toxic metals such as cadmium or other heavy metals), preferred salts include sodium chloride, potassium acetate, sodium acetate, ammonium acetate, ammonium chloride, ammonium sulfate or potassium chloride, most preferably ammonium sulfate. Salt is added to the suspension at a concentration of about 100–500 mM, preferably about 200–400 mM; and most preferably about 300 mM. The salt should be gradually added to the solution to provide for optimal solubilization. Following addition, of the salt, the solution is mixed for about an additional 30–60 minutes, most preferably about an additional 45 minutes, during which time the bacterial cells are converted into spheroplasts or protoplast and the intracellular proteins, including reverse transcriptase enzymes, begin to cross the spheroplast or protoplast membrane while cellular nucleic acids are preferably retained within the spheroplast or protoplast.

Microfiltration, Concentration and Diafiltration

Following lpermeabilization of the cells, reverse transcriptases are collected by subjecting the spheroplasts or protoplast to filtration (e.g., microfiltraiton) to separate the enzymes from the spheroplasts or protoplast and remove particulate matter. In another aspect, the filtrate may be subjected to concentration and/or diafiltration. The present methods obviates the need for precipitation of nucleic acids and/or the use of centrifugation techniques; this elimation of centrifugation facilitates the rapid production of reverse transcriptase enzymes at any scale in a continuous or discontinuous fashion. The general methods of filtration (e.g., microfiltration), concentration and diafiltration are generally well-known to one of ordinary skills, and will re:sult in the preparation of an enzyme ultrafiltrate (which is preferably nucleic-acid free) suitable for purification and characterization of the enzymes.

Microfiltration is preferably carried out by collecting the spheroplast/or protoplast solution in permeabilization buffer (described above) and diafiltering the solution against a filtration buffer thorugh a semi-permeable membrane, most preferably a hydrophilic dialysis, microfiltration or ultrafiltration membrane. The filtration buffer preferably is a dH$_2$O-based soltion comprising: a) a buffer salt, preferably trishydroxymethylaminomethane (TRIS base) at a concentration of about 25–500 mM, preferably about 50–250 mM, more preferably about 50–150 mM, and most preferably about 100 mM, at a pH of about 7.0–9.0, preferably about 7.0–8.5, more preferably about 7.0–8.0, and most preferably about 8.0 (pH at 4° C.); and b) the protein-extracting salt which was added to the permeabilization buffer, which is preferably ammonium sulfate, at a concentration of about 100–500 mM, preferably about 200–400 mM, and most preferably about 300 mM. The filtration buffer solution may also comprise other components, such as protease inhibitors (e.g., phenylmethylsulfonylfluoride, added at a final concentration of about 1.0 mM), reducing agents (e.g., β-mercaptoethanol or most preferably dithiothreitol at a final concentration of about 1 mM), and chelating agents (e.g., disodium ethylenediaminetetraacetic acid ($Na_2EDTA$), most preferably at a concentration of about 10 mM; this buffer composition is referred to hereinafter as "filtration buffer." It will be understood by one of ordinary skill in the art, however, that other suitable buffer compositions may be substituted with equivalent effect in the filtration process.

Preferable for use in microfiltration is a system allowing permeation of intracellular enzymes through the membrane and into the filtrate, leaving spheroplasts and/or protoplast (with the nucleic acids retained therein) and particulate matter in the retentate. One suitable system providing such conditions is, for example, a hollow fiber microfiltration system which is commercially available (Spectrum), although similar systems providing the same results will be known to one of ordinary skill. Following microfiltration in this manner, the filtrate contains the reverse transcriptase enzymes which are substantially free of nucleic acids such as DNA, as the DNA is partitioned from the enzymes by being retained with the particulate matter. This filtrate may then be concentrated, for example by membrane concentration through a semi-permeable membrane using a commercially available system (AG/Technology Corp.) or equivalent. The enzymes may then be individually purified from the concentrate as described below; alternatively, the concentrate may be diafiltered as described above against a suitable buffer solution to place the enzymes into an appropriate chemical environment for purification, as described in more detail in Example 2.

Purification and Characterization of Enzymes

Following concentration and/or diafiltration as described above, reverse transcriptase enzymes may be purified by a variety of protein purification techniques that are well-known to one of ordinary skill in the art. Suitable techniques for purification include, but are not limited, ammonium sulfate or ethanol precipitation, acid extraction, preparative gel electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography, lectin chromatography, and immobilized metal affinity chromatography (IMAC). Most preferably, the enzymes are purified by a. combination of liquid chromatographic techniques including ion exchange, affinity and size exclusion methods such as those described in Example 3, although alternative chromatographic solid supports, mobile phases and associated methods may be equivalently used and will be well-known to one of ordinary skill. The invention thus provides for substantially pure reverse transcriptases. Substantially pure a used herein refers to a preparation or sample which is substantially free of contaminating components, proteins etc. which may adversely affect the activity or performance of the RT in the use of the enzyme such as in amplification or synthesis.

Assays for Nucleic Acid Content

Purified reverse transcriptase enzymes made according to the present invention may be examined for nucleic acid content by a variety of methods which are well-known to one of ordinary skill in the art. For example, a sample of the final product can be assayed by ultraviolet spectrophotometry, comparing absorption of light by the sample at a wavelength of 260 nm ($A_{260}$, the absorption maximum for DNA) to that at 280 nm ($A_{280}$, the absorption maximum for tryptophan, which is found in most proteins); the lower the $A_{260}/A_{280}$ ratio, the lower the content of DNA in the sample. Samples with minimal $A_{260}/A_{280}$ values may then be pooled to constitute a substantially nucleic acid-free preparation of reverse transcriptase enzymes.

Alternatively, samples may be directly assayed for the presence of DNA or other nucleic acids by gel electrophoresis or dot blotting and staining with a DNA-binding dye (e.g., ethidium bromide, acridine orange, Hoechst stain, pico green) or antibody, which are commercially available, for example, from Sigma (St. Louis, Mo.). In addition, the DNA content of samples of reverse transcriptases may be examined by carrying out an amplification reaction in the absence of exogenously added DNA template, either as a "no-template control" in a standard PCR assay (Rand, K. H., and Houck, H., *Mol. Cell Probes* 4(6):445–450 (1990)), or by specifically designing an assay to measure DNA content by radiolabeled nucleotide incorporation into salmon testes or bovine thymus DNA, according to methods that are starftlard in the art. Use of such assays will allow one of ordinary skill, without undue experimentation, to identify samples of reverse transcriptase enzymes obtained by the purification schemes described above, which may then be pooled and used as preparations of substantially nucleic acid-free reverse transcriptase enzymes.

Formulation of Enzymes

Following their purification or isolation, the substantially pure and preferably substantially DNA-free reverse transcriptase enzymes may be stored until use in a buffered solution at temperatures of about $-\phi 80°$ to 25° C., most preferably at −80° to 4° C., or in lyophilized form. Alternately, the enzymes may be stabilized by drying in the presence of a sugar such as trehalose (U.S. Pat. Nos. 5,098,893 and 4,824,938) or acacia gum, pectin, carboxymethylcellulose, carboxymethylhydroxyethylcellulose, guar, carboxy guar, carboxymethylhydroxypropyl guar, laminaran, chitin, alginates or carrageenan. In addition, the enzymes provided by the present invention may be directly formulated into compositions to be used in techniques requiring the use of reverse transcriptase enzymes, such as compositions for nucleic acid synthesis or amplification.

Kits

In other preferred embodiments, the substantially pure and preferably substantially DNA-free reverse transcriptases provided by the present invention may be assembled into kits for use in methods requiring reverse transcriptase enzymes, such as nucleic acid synthesis (e.g., cDNA synthesis), amplification (e.g., RT-PCR) or sequencing utilizing RT. The kit according to the present invention comprises a carrier means having in close confinement therein one or more container means, such as vials, tubes, bottles and the like, wherein a first container means contains a reverse transcriptase of this invention. The kit encompassed by this aspect of the present invention may further comprise in the same or different containers additional reagents and compounds necessary for carrying out standard nucleic synthesis, amplification and sequencing protocols. Such additional components may include reaction buffers, nucleotides (e.g., dTTP, DATP, dCTP, dGTP, ddATP, ddTTP, ddGTP, ddCTP and derivatives thereof including labeled nucleotides), one or more DNA polymerases (such as Taq DNA polymerase), one or more primers and the like.

Use of the Reverse Transcriptase Enzymes

The substantially pure or substantially DNA-free reverse transcriptase enzymes and kits embodied in the present invention will have general utility in any application utilizing reverse transcriptase enzymes, including but not limited to nucleic acid cDNA synthesis, and nucleic acid amplification or sequencing methodologies.

In a first aspect, the RTs of the invention may be used for synthesis of nucleic acid molecules. Such methods for making one or more nucleic acid molecules, comprising mixing one or more nucleic acid templates (preferably one or more RNA templates and most preferably one or more messenger RNA templates) with one or more polypeptides having reverse transcriptase activity and incubating the mixture under conditions sufficient to make a first nucleic acid molecule or molecules complementary to all or a portion of the one or more nucleic acid templates. In a preferred embodiment, the first nucleic acid molecule is a single-stranded cDNA. Nucleic acid templates suitable for reverse transcription according to this aspect of the invention include any nucleic acid molecule or population of nucleic acid molecules (preferably RNA and most preferably mRNA), particularly those derived from a cell or tissue. In a preferred aspect, a population of mRNA molecules (a number of different mRNA molecules, typically obtained from cells or tissue) are used to make a cDNA library, in accordance with the invention. Preferred cellular sources of nucleic acid templates include bacterial cells, fungal cells, plant cells and animal cells.

RT enzymes made in accordance with the invention may also be used in methods for amplifying and sequencing nucleic acid molecules. Nucleic acid amplification methods according to this aspect of the invention may be one step (e.g., one-step RT-PCR) or two-step (e.g., two-step RT-PCR) reactions. According to the invention, one-step RT-PCR type reactions may be accomplished in one tube thereby lowering the possibility of contamination. Such one-step reaction comprise (a) mixing a nucleic acid template (e.g., mRNA) with one or more polypeptides having reverse transcriptase activity and with one or more DNA polymerases and (b) incubating the mixture under conditions sufficient to amplify a nucleic acid molecule complementary to all or a portion of the template with one or more polypeptides having reverse transcriptase activity (and optionally having DNA polymerase activity). Incubating such a reaction mixture under appropriate conditions allows amplification of a nucleic acid molecule complementary to all or a portion of the template. Such amplification may be accomplished by the reverse transcriptase activity alone or in combination with the DNA polymerase activity. Two-step RT-PCR reactions may be accomplished in two separate steps. Such a method comprises (a) mixing a nucleic acid template (e.g., mRNA) with one or more reverse transcriptases, (b) incubating the mixture under conditions sufficient to make a nucleic acid molecule (e.g., a DNA molecule) complementary to all or a portion of the template, (c) mixing the nucleic acid molecule with one or sore DNA polymerases and (d) incubating the mixture of step (c) under conditions sufficient to amplify the nucleic acid molecule. For amplification of long nucleic acid molecules (i.e., greater than about 3–5 Kb in length), a combination of DNA polymerases may be used, such as one DNA polymerase having 3' exonuclease activity and another DNA polymerase being substantially reduced in 3' exonuclease activity. An alternative two-step procedure comprises the use of one or more polypeptides having reverse transcriptase activity and DNA polymerase activity (e.g., Tth, Tma or Tne DNA polymerases and the like) rather than separate addition of a reverse transcriptase and a DNA polymerase.

Nucleic acid sequencing methods according to this aspect of the invention may comprise both cycle sequencing (sequencing in combination with amplification) and standard sequencing reactions. The sequencing method of the invention thus comprises (a) mixing a nucleic acid molecule to be sequenced with one or more primers, two or more reverse transcriptases, one or more nucleotides and one or more terminating agents, (b) incubating the mixture under conditions sufficient to synthesize a population of nucleic acid molecules complementary to all or a portion of the molecule to be sequenced, and (c) separating the population to determine the nucleotide sequence of all or a portion of the molecule to be sequenced. According to the invention, one or more DNA polymerases (preferably thermostable DNA polymerases) may be used in combination with or separate from the reverse transcriptases.

Amplification methods in which the present enzymes may be used include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822). Nucleic acid sequencing techniques which may employ the present enzymes include dideoxy sequencing methods such as those disclosed in U.S. Pat. Nos. 4,962,022 and 5,498,523, as well as more complex PCR-based nucleic acid fingerprinting techniques such as Random Amplified Polymorphic DNA (RAPD) analysis (Williams, J. G. K., et al., *Nucl. Acids Res.* 18(22):6531–6535, 1990), Arbitrarily Primed PCR (AP-PCR; Welsh, J., and McClelland, M., *Nucl. Acids Res.* 18(24): 7213–7218, 1990), DNA Amplification Fingerprinting (DAF; Caetano-Anolles et al., *Bio/Technology* 9:553–557, 1991) microsatellite PCR or Directed Amplification of Minisatellite-region DNA (DAMD; Heath, D. D., et al., *Nucl. Acids Res.* 21(24):5782–5785, 1993), and Amplification Fragment Length Polymorphism (AFLP) analysis (EP 0 534 858; Vos, P., et al., *Nucl. Acids Res.* 23(21):4407–4414, 1995; Lin, J. J., and Kuo, J., *FOCUS* 17(2): 66–70, 1995). In particular, the enzymes and kits of the present invention will be useful in the fields of medical therapeutics and diagnostics, forensics, and agricultural and other biological sciences, in any procedure utilizing reverse transcriptase enzymes.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Permeabilization of Bacterial Cells

In the initial steps of the purification process, 20 kg bacterial cells (*E. coli*, N4830 (pRT601) (see U.S. Pat. No. 5,017,492; ATCC deposit no. 67007) containing the expression vector for MMLV-RT which were obtained directly from actively growing cultures were suspended at 250 g of cells/L into cold (4° C.) perm eabilization buffer (100 mM BisTRIS, 5.0% Triton X-100, 2.0% sodium deoxycholic acid, 10 mM EDTA, 1 mM dithiothreitol (DTT), pH 7.0.

During suspension of the cells in the buffer, phenylmethylsulfonylfluoride (PMSF) was added to a final concentration of 1.0 mM. Cells were stirred for about 45 minutes at 4° C. to ensure complete suspension, and then ammonium sulfate was added to a final concentration of 300 mM and the cell suspension was stirred for an additional 45 minutes. During this time, cells were permeabilized via the action of the deoxycholic acid and Triton X-100, and intracellular protein release into the buffer was enhanced by the action of the ammonium sulfate.

Example 2

Microfiltration, Concentration and Diafiltration of Extracts

Microfiltration of the suspension was then carried out through 120 ft$^2$ 0.2 μm Microgon mixed ester cellulose hollow fiber system, using a recirculation rate of 120 L/min. The suspension was diafiltered with five to six volumes of cold filtration buffer, collecting the permeate in a suitable sized chilled (4° C.) container. Under these conditions, recombinant enzymes passed through the membrane with the permeate, leaving the bacterial cells in the retentate.

As the ultrafiltration proceeded, concentration of the permeate was begun once a sufficient volume had been collected to prime the second ultrafiltration system. Permeate was concentrated using an Amicon DC-90 system, through an AG technologies 10,000 MWCO membrane (although alternative membrane systems of 10,000 MWCO, such as a Filtron system, a Millipore plate and frame system, or a membrane from Microgon may be also used) and an in-line chiller to minimize heat build-up from the pumping system. Permeate was concentrated to approximately the original volume of the extract (see Example 1), and was then diafiltered against about seven volumes of diafiltration buffer (20 mM NaPi, 100 mM NaCl, 10.0 mM EDTA, 1 mM DTT, pH 6.5), until the conductivity was <7 mS. Ultrafiltrate was then immediately used for purification of the enzyme (Example 3).

Example 3

Purification and Characterization of DNA-free Enzyme

Purification of the enzyme from the ultrafiltrate was accomplished by a series of chromatographic steps, using a procedure modified slightly from that described for purification of T5 DNA polymerase from *E. coli* (Hughes, A. J., Jr., et al., *J. Cell Biochem. Suppl.* 0 16(Part B):84 (1992)).

A. Macroprep High S

The filtrate was mixed with 9L Whatman DE-52 and then was polish filtered through two CUNO 8ZP 10 A depth filters. In the first chromatographic step, the ultrafiltrate was applied to a 9L BioRad Macroprep High S. The column was then washed with 10 volumes of 20 mM TRIS, 150 mM NaCl, 0.1 mM EDTA, 10% glycerol, 0.01% Triton X-100, 1 mM DTT, pH 8.0 at 4.0° C. run at a flow rate of about 20 cm/hr. Product elution was effected with a ten column volume gradient of the wash buffer to this same buffer containing 800 mM NaCl w/o EDTA run at 10 cm/hr. Fractions demonstrating at least ⅓ of the large UV peak were pooled and subjected to further purification.

B. Macroprep Ceramic CHT

Pooled eluate from the High S Column was applied at a flow-rate of 20 cm/hr to a 6L column of Macroprep Ceramic CHT, and the column was then washed with 5 volumes of 20 mM potassium phosphate, 100 mM KCl, 10% glycerol, 0.01% Triton X-100, 1 mM DTT, pH 7.0 at 4° C. at a flow-rate of 10 cm/hr. Fractions showing at least ⅕ of the UV peak were pooled and subjected to further purification.

C. Fractogel COO-Column

The pool from the Ceramic HTP column was diluted with an equal volume of 100 mM TRIS, 100 mM NaCl, 0.2 mM EDTA, 30% glycerol, 0.01% Triton X-100, 1 mM DTT, pH 7.5 at 4.0° C. and applied at a flow rate of 20 cm/hr to a Fractogel COO-column (E. Merck, Inc.), which concentrates the product. The column was then washed with 2 column volumes of low salt Fractogel COO-buffer (20 mM TRIS, 100 mM NaCl, 20% glycerol, 0.1 mM EDTA, 0.01% Triton X-100, 1 mM DTT, pH 7.5), and the enzyme eluted with 50% high salt ceramic Fractogel COO-buffer (20 mM TRIS, 400 mM NaCl, 0.1 mM EDTA, 20% glycerol, 0.01% Triton X-100, 1.0 mM DTT, pH 7.5 at 4.0° C. at 20 cm/hr, and fractions containing the UV peak were collected, and pooled as described above.

D. Dialysis

Fractogel COO-pool was dialyzed against 20 volumes of dialysis buffer (20 mM TRIS, 0.1 mM EDTA, 50% (vol/vol) glycerol, 100 mM NaCl, 0.01% Triton X-100, 1 mM DTT, pH 7.5) for 24 hours. Purified enzyme bulk was then stored at −20° C. until used.

E. DNA Contamination Assays

To determine the extent of DNA contamination of various preparations of RT, samples of RT obtained from commercial sources may be compared to a preparation made according to the methods of the present invention in a polymerase assay similar to that outlined above, except that no salmon testes DNA template is included in the reaction mixture. Briefly, reaction mixtures (500 μl) containing 25 mM TAPS (pH 9.3), 10 mM MgCl$_2$, 50 mM KCl, 1 mM DTT, 100 μM each of dATP, dTTP, dGTP and dCTP, and 600 cpm of [$^3$H]dTTP/pmol of total nucleotide are prepared and pre-incubated at 72° C. for five minutes. 100 units of M-MLV RT are added to the reaction mixtures and then 100 units of purified DNA-free Taq DNA polymerase (see U.S. Pat. No. 5,861,295) are added at specific time intervals to initiate the reaction. A 30 μl sample is removed and added to a vial containing 5 μl of 500 mM EDTA on ice. Once all time points are collected, a 20 μl aliquot of the quenched reaction sample is applied to a GF/C filter, which is washed, dried and counted as described above. Results are expressed as $^3$H incorporation (cpm) at each time point.

Other commercially available preparations of RT may be compared to the preparations provided by the present invention for their DNA content. Together, the results should indicate that preparations of RT provided by the present invention are substantially free of nucleic acids, while several commonly used commercial preparations of RT contain substantial amounts of contaminating DNA.

Having now fully described the present invention in some detail by way of illustration and example for purposes of clarity of understanding, it will be understood by those of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications cited herein are indicative of the level of skill of those skilled in the art to which this invention pertains, and are herein incorporated by reference in their entirety.

What is claimed is:

1. A method of isolating or purifying a reverse transcriptase, said method comprising permeabilizing a cellular source of reverse transcriptase, subjecting said permeabilized cellular source of reverse transcriptase to filtration, and isolating said reverse transcriptase.

2. The method of claim 1, wherein said reverse transcriptase is substantially free of nucleic acids.

3. The method of claim 1, wherein said cellular source is a bacterial cell or a recombinant bacterial cell.

4. The method of claim 3, wherein said permeabilization forms spheroplasts and/or protoplasts.

5. The method of claim 4, wherein said filtration comprises microfiltration and/or ultrafiltration.

6. The method of claim 1, wherein said permeabilization is accomplished by contacting said cellular source with an aqueous solution comprising at least one component selected from the group consisting of a chaeotropic agent and a nonionic detergent.

7. The method of claim 6, wherein said nonionic detergent is selected from the group consisting of Triton X-100 and sodium deoxycholic acid.

8. The method of claim 6, wherein said permeabilizing is carried out in the presence of a buffer comprising bis-trishydroxymethylaminomethane (BisTRIS®), octylphenoxypolyethoxyethanol (Triton X-100®), sodium deoxycholic acid, ethylenediaminetetraacetic acid (EDTA), and dithiothreitol.

9. The method of claim 1, wherein said isolation step comprises column chromatography.

10. The method of claim 1, wherein said method is conducted under conditions favoring the partitioning of nucleic acids from said reverse transcriptase.

11. The method of claim 10, wherein said conditions comprise microfiltration of spheroplast or protoplasts in the presence of ammonium sulfate.

12. The method of claim 1, wherein said reverse transcriptase is M-MLV RT or M-MLV RT substantially reduced in RNase H activity.

13. The method of claim 1, wherein said isolating is accomplished by ion exchange chromatography.

14. The method of claim 13, wherein said chromatography is carried out with a strong cation exchanger column, a ceramic hydroxylapatite column, or a carboxyl anion column.

15. The method of claim 1, wherein said isolating is accomplished by dialysis.

16. The method of claim 1, wherein said reverse transcriptase is substantially reduced in RNase H activity.

17. The method of claim 16, wherein said reverse transcriptase is selected from the group consisting of MMLV, RSV, AMV, RAV, MAV, and HIV reverse transcriptases.

18. The method of claim 1, wherein said reverse transcriptase is selected from the group consisting of MMLV, RSV, AMV, RAV, MAV, and HIV reverse transcriptases.

* * * * *